United States Patent [19]
Mercado

[11] Patent Number: 5,304,138
[45] Date of Patent: Apr. 19, 1994

[54] SINGLE USE, DESTRUCTIBLE MEDICAL SYRINGE

[75] Inventor: Alexander D. Mercado, Hicksville, N.Y.

[73] Assignee: Advanced Safety Technology, Hicksville, N.Y.

[21] Appl. No.: 947,131

[22] Filed: Sep. 18, 1992

[51] Int. Cl.⁵ .............................................. A61M 5/00
[52] U.S. Cl. .................................... 604/110; 604/218
[58] Field of Search ............... 604/110, 187, 192, 218, 604/220

[56] References Cited

U.S. PATENT DOCUMENTS 5,114,405 5/1992 Winter ................................ 604/110

FOREIGN PATENT DOCUMENTS 2197792 6/1988 United Kingdom ................ 604/110

Primary Examiner—John D. Yasko
Attorney, Agent, or Firm—Bauer & Schaffer

[57] ABSTRACT

There is disclosed a single use, destructible, medical syringe in which the barrel and plunger are provided with structural elements which break of a portion of the plunger or lock the plunger in place in the barrel after an initial use. The syringe is simple in structure and made of a plastic, such as polyethylene.

10 Claims, 2 Drawing Sheets

SINGLE USE, DESTRUCTIBLE MEDICAL SYRINGE

This invention relates to syringes. More particularly, the invention relates to medical syringes for intravenous and other injections which self-destruct after an initial use and thus are used only once.

BACKGROUND OF THE INVENTION

As is well-known, the repetitious use of medical syringes without proper sterilization is in a large part responsible for the tragic spread of diseases, such as AIDS and Hepatitis B, among others. This problem has resulted in the attempted development of disposable syringes which are produced and made available to anyone requesting them. Unfortunately, these so-called "disposable" syringes are disposable in theory only and, in actual practice, are readily capable of re-use, as are conventional syringes. Moreover, since sterilization of reusable syringes requires special equipment and is time consuming and expensive, the use of the cheaper and so-called expendable disposable syringes has proliferated.

Syringes intended for a single use are also known. A wide variety of such syringes have been developed. However, most of them are complex in structure and thus, expensive to make. For example, one such device comprises a combined ampoule and syringe in which the piston or plunger is provided with a joint at the end placed inside the cylinder of the syringe. The joint, which is separable from the piston, is designed to remain in its final position at the bottom of the cylinder when the injection is completed. Other such devices of this sort have other drawbacks.

There exists, therefore, a need for a single use, destructible, medical syringe which does not exhibit the disadvantages and drawbacks of the known disposable syringes. The present invention fulfills such a need.

BRIEF STATEMENT OF THE INVENTION

In accordance with the present invention there is provided a single use, destructible, medical syringe comprising a barrel, to which a needle is connectable at one end and a plunger is disposable through the opposite end. Mounted at the inner end of the plunger is a seal member. The barrel of the syringe is provided with a countersunk portion between the open end and the needle-bearing end. Located above the continuing portion is means for preventing withdrawal of the plunger in an intact condition, so that after initial use of the syringe any movement of the plunger to refill the syringe is prevented.

THE DRAWINGS

In order to understand the invention more fully, reference is made to the accompanying Drawings which are to be taken in conjunction with the following detailed description of the preferred embodiments of the invention and in which Drawings.

DESCRIPTION OF THE PREFERRED EMBODIMENTS

Figure 1:
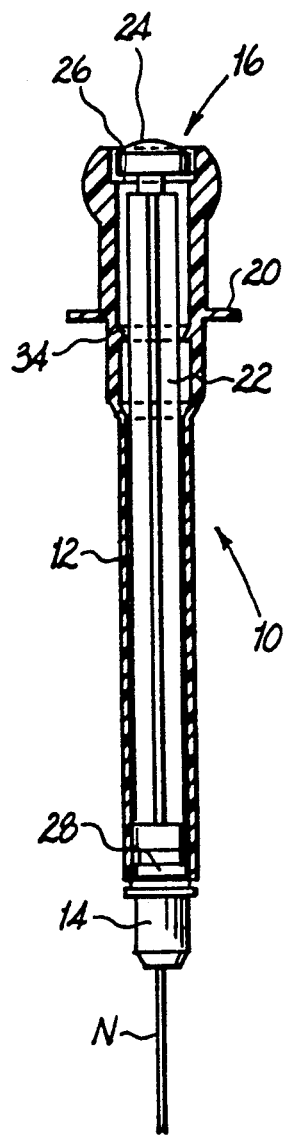
FIG. 1 is a front view in section of a medical syringe of one embodiment according to the invention showing the construction of the barrel and plunger disposed therein.

Referring now to FIG. 1 syringe embodying the invention is generally depicted by the numeral 10. The syringe is formed of a barrel 12 which may be of circular cross section and at least in its interior of uniform diameter. At the far end of the barrel 12 there is provided a fitting 14 to which a needle N is attached. The opposite or open end of the barrel generally depicted by the numeral 16 is formed within an enlarged portion 18 having an outwardly extending rim 20 for supporting the syringe between the fingers of the user. A plunger 22, having a cap 24, extends through the opening into the barrel 12. The interior of the opening is provided with a stepped shoulder 26 against which the cap 24 may rest when the plunger is fully inserted into the barrel.

Figure 1A:
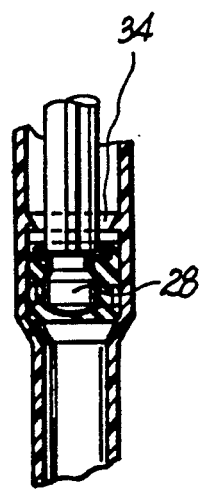
FIG. 1A is an enlarged view of the lower end of the syringe of FIG. 1 showing frangible rubber seal disposed on the end of the plunger in the vicinity of the needle bearing portion of the barrel.
Figure 1B:
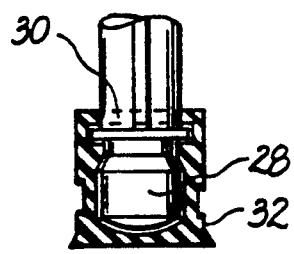
FIG. 1B is an enlarged view of the upper end of the syringe showing the means for separating the frangible seal from the plunger.

As seen in FIGS. 1A and 1B the far end of the plunger 22 is provided with an outwardly extending boss 28 which is weakened as shown by broken lines 30 so that the boss 28 is frangible. Mounted on the box 28 is a cap seal 32 forming a piston head slidable on the inner surface of the barrel. Disposed on the internal surface of the barrel just below the finger rim 20 is a countersunk portion thereof is an inwardly directed circumferential lip 34 adapted to engage the end of the cap seal 32 when the plunger is withdrawn (FIG. 1B) thereby preventing withdrawal of the plunger from the barrel and destruction of the frangible boss 28. Consequently, although the syringe is manufactured and filled with medication or the like to be dispensed therefrom, it cannot be re-used since when the user withdraws the plunger for purposes of refilling the syringe the lip 34 will cause the boss 28 carrying the seal to be broken away, thus preventing further use of the syringe.

Figure 2:
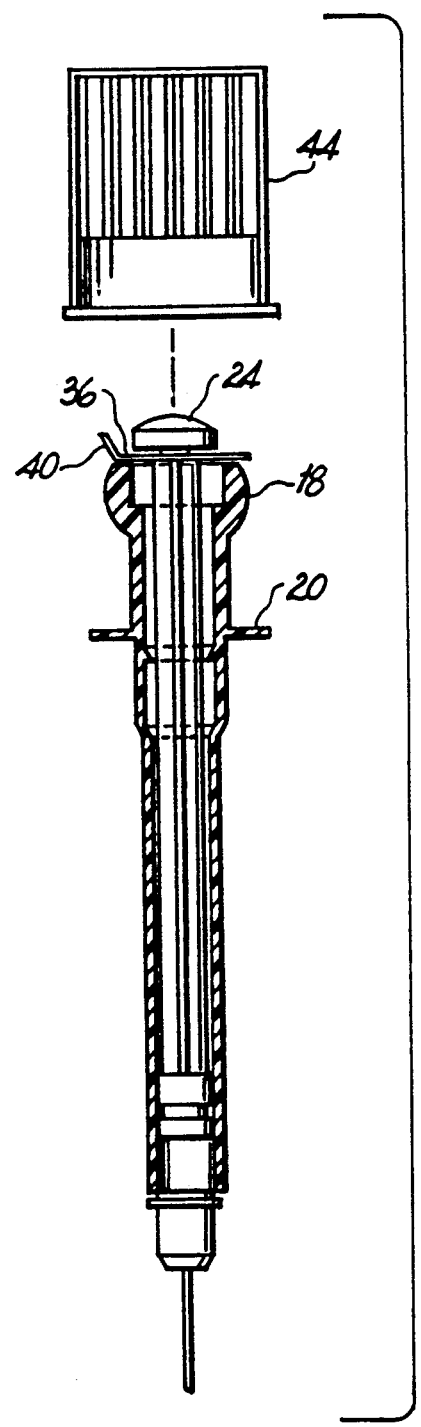
FIG. 2 is a modification of the syringe illustrated in FIG. 1 employing a safety clip disposed between the lower surface of the cap of the plunger and the open end of the barrel.
Figure 3:
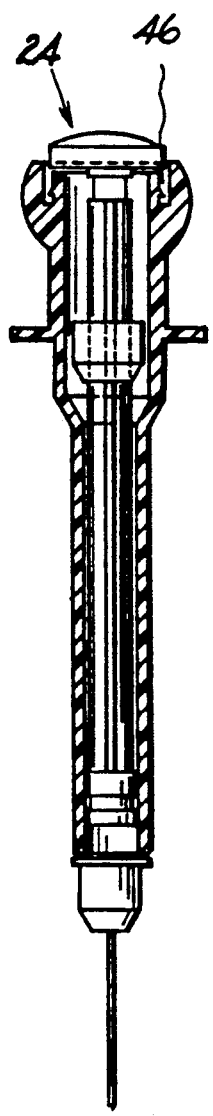
FIG. 3 is a frontal elevational view in section of a modification of a syringe according to the invention.
Figure 4:
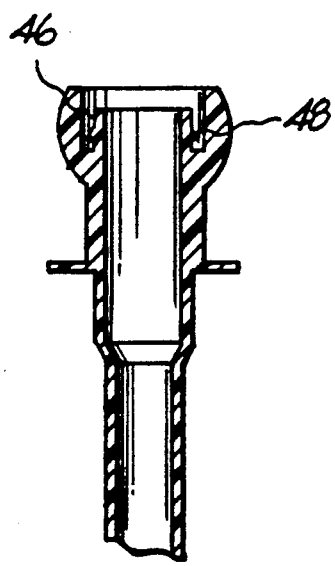
FIG. 4 is a partial front view in section of an illustration of another embodiment of the syringe of the invention showing a qualification in which the barrel is provided with a modified open end and modified cap on the plunger which locks the plunger in place after initial use of the syringe.
Figure 6:
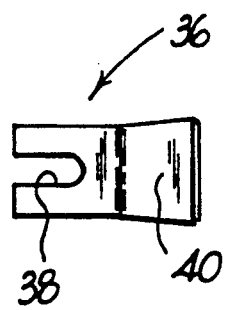
FIG. 6 is a plan view of the safety lock.

The syringe is provided with a U-shaped safety clip 36, FIG. 6, having a slot 38 provided and an upwardly extending gripping member 40. The safety clip 36 is adapted to be disposed between the lower surface of the plunger cap 24 and the upper surface of the enlarged portion 18 of the barrel end (as in FIG. 2) to hold the plunger in a deactivated position and prevent the plunger from being prematurely depressed until the clip is removed from position.

All of the described elements except for the rubber seal may be made of rigid plastic, such as nylon, polyurethane and polyethylene or the like. Of the materials, polyethylene is preferred. While the seal is preferably made of rubber, it is within the purview of this invention to make it of any similar material such as silicone rubber, for example. If desirable, the syringe shown in FIG. 2 may also be provided with a cover 44 which fits over the open end 16 of the barrel and rests on finger rim 20 of the barrel.

The embodiment illustrated in FIGS. 3 through 6 provides additional features which prevent re-use by locking the plunger in place once it has been pushed into the barrel in addition to the breaking of the frangible seal.

Referring next to FIGS. 3 through 6 it is seen that the enlarged open end cup-like portion of the barrel is provided with an internal recess 46. The internal surface of the recess has an outwardly directed flange 48 located thereon while the cap 21 of is provided with a depending peripheral skirt 50 having an inwardly directed flange 52 which passes over the boss 48 when the plunger is moved into the barrel into locking engagement with the flange 48 of the recess. This locks the plunger into the barrel and prevents further use of the syringe.

In addition a sleeve 54, preferably of rubber, is located within the barrel above the countersunk portions. Sleeve 54 is bonded to the internal surface by sonic welding. Thus, should the locking features of the cap and cup like portion fail, the sleeve 54 will prevent withdrawal of the plunger and break the frangible end of the plunger with the rubber seal and thus prevent reuse of the syringe. A needle guard (not shown) may also be employed.

Figure 7A:
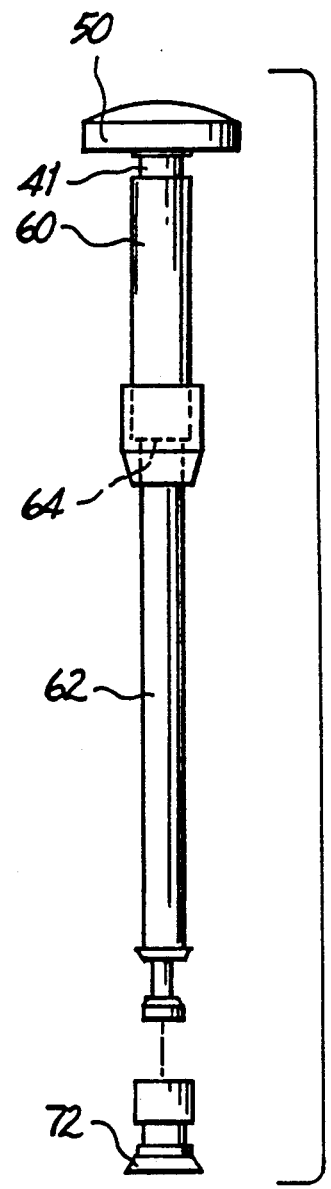
FIGS. 7a and 7b are views of a modified plunger and sleeve.
Figure 7B:
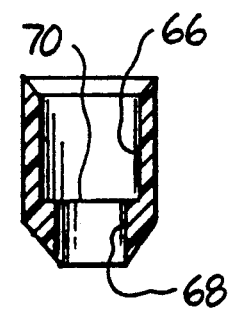

In FIGS. 7a and 7b, a modified plunger is shown to have an upper section 60 of a larger outer diameter than the lower section 62. As a result, a shoulder 64 is formed between the sections. Slidably disposed over the interfacing shoulder 64 is a sleeve having self conforming diameter sections 66 and 68 with an inward shoulder 70. An elastic seal piston head 72 is attached at the end of the lower piston rod. Otherwise, the structure is the same and functions in the same manner as previously described.

Figure 5:
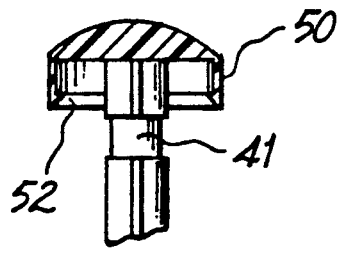
FIG. 5 is a partial, exploded, sectional view of the syringe illustrated in FIG. 3 showing the enlarged open end of the barrel in detail.

It will be apparent that with very little additional structure, a truly single use syringe is formed. The internal plunger and plunger head will be automatically broken upon any attempt to withdraw the plunger, preparatory to refilling the barrel. Ancillary features reside in providing for a safety lock preventing premature ejection of the contents of the barrel (FIG. 2) and/or freedom of movement of the plunger once the syringe has been emptied (FIGS. 5 and 6).

While various modifications and changes have been disclosed, others will be obvious to the reader. Accordingly, the present disclosure should be taken as illustrative only and not limiting of the scope of the invention.

What is claimed is:

1. A single use, destructible medical syringe comprising a barrel provided with a needle or adapted for connection to a needle at one end, an opposite open end, and a plunger disposed in said barrel, said plunger provided with a cap at the end thereof nearest the open end of said barrel and a frangible seal attached to the opposite end, said barrel having a countersunk portion extending from the vicinity of the open end towards the needle-bearing end thereof, and means for preventing withdrawal of said plunger intact from said barrel comprising a boss extending around the internal surface of said barrel above said countersunk portion, bearing against said seal to break the seal upon withdrawal of the plunger, whereby after initial use further use of said syringe is prevented.

2. A single use, destructible medical syringe according to claim 1 including a clip comprising a base member having an open notch therein, said notch disposed around the external surface of the plunger between the lower surface of the cap thereof and the open end of the barrel of said syringe.

3. A single use, destructible medical syringe according to claim 1 including a needle guard disposed on the barrel at the needle-bearing end of said syringe.

4. A single use, destructible, medical syringe according to claim 1 including a cover disposed on the barrel at the open end thereof.

5. A single use, destructible, medical syringe according to claim 1 wherein the open end of the barrel is provided with an enlarged cup-like portion having an internal groove therein, the internal surface of said groove having an outwardly divided boss located thereon, the cap of the plunger being provided with a depending peripheral skirt provided with an inwardly directed edge which passes over said boss when said plunger is moved into said barrel, whereby after an initial use contact between said boss and the inwardly directed skint locking said plunger into said barrel and preventing further use of said syringe.

6. A single use, destructible, medical syringe according to claim 5 including a sleeve located in the barrel above the countersunk portion of said barrel.

7. A single use, destructible, medical syringe according to claim 1 wherein the barrel and the plunger are made of plastic.

8. A single use, destructible, medical syringe according to claim 7 wherein the plastic is polyethylene.

9. A single use, destructible, medical syringe according to claim 1 wherein the seal is made of rubber.

10. A single use, destructible, medical syringe according to claim 6 wherein the sleeve is made of rubber.

* * * * *